US006970531B2

(12) United States Patent
Eberhard et al.

(10) Patent No.: US 6,970,531 B2
(45) Date of Patent: Nov. 29, 2005

(54) CONTINUOUS SCAN RAD TOMOSYNTHESIS SYSTEM AND METHOD

(75) Inventors: Jeffrey Wayne Eberhard, Albany, NY (US); Bernhard Erich Hermann Claus, Niskayuna, NY (US); Abdulrahman Abdallah Alkhalidy, Clifton Park, NY (US); James Talmage Dobbins, III, Durham, NC (US); Devon James Godfrey, Durham, NC (US)

(73) Assignees: General Electric Company, Niskayuna, NY (US); Duke University, Durham, NC (US)

(*) Notice: Subject to any disclaimer, the term of this patent is extended or adjusted under 35 U.S.C. 154(b) by 20 days.

(21) Appl. No.: 10/265,488

(22) Filed: Oct. 7, 2002

(65) Prior Publication Data

US 2004/0066882 A1 Apr. 8, 2004

(51) Int. Cl.$^7$ .............................................. H05G 1/60
(52) U.S. Cl. ........................ 378/26; 378/21; 378/22; 378/25; 378/197
(58) Field of Search ................... 378/21–27, 197, 378/2, 196

(56) References Cited

U.S. PATENT DOCUMENTS

| 4,211,927 | A | * | 7/1980 | Hellstrom et al. ............. 378/26 |
| 4,340,816 | A | * | 7/1982 | Schott .......................... 378/22 |
| 5,583,904 | A | | 12/1996 | Adams ......................... 378/22 |
| 5,627,868 | A | | 5/1997 | Nobuta et al. ................. 378/19 |
| 6,028,910 | A | * | 2/2000 | Kirchner et al. .............. 378/22 |
| 6,069,933 | A | * | 5/2000 | Schultz ........................ 378/62 |
| 6,081,577 | A | | 6/2000 | Webber ........................ 378/23 |
| 6,173,033 | B1 | * | 1/2001 | Klingenbeck-Regn et al. ............................ 378/20 |
| 6,196,715 | B1 | | 3/2001 | Nambu et al. ............... 378/191 |
| 6,216,540 | B1 | | 4/2001 | Nelson et al. ................ 73/633 |

(Continued)

FOREIGN PATENT DOCUMENTS

EP 0 405 862 6/1990

(Continued)

OTHER PUBLICATIONS

"Description of a Digital Tomosynthesis (DTS) System," Murry, Jr., et al., SPIE Proc. 419, pp. 175-183 (1983).

(Continued)

*Primary Examiner*—Allen C. Ho
(74) *Attorney, Agent, or Firm*—Jean K. Testa; Christian G. Cabou

(57) ABSTRACT

An imaging system for performing tomosynthesis on a region of an object comprises an x-ray source, motion controller, an x-ray detector and a processing unit. The x-ray source is positioned at a predetermined distance from the object and continuously moves along a linear path relative to the object. The x-ray source transmits x-ray radiation through the region of the object at a plurality of predetermined locations. The motion controller is coupled to the x-ray source and continuously moves the x-ray source along the path relative to the object. The x-ray source minimizes vibration in the imaging system due to continuous movement. The x-ray detector is positioned at a predetermined distance from the x-ray source and detects the x-ray radiation transmitted through the region of the object, thus acquiring x-ray image data representative of the region of the object. The processing unit is coupled to the x-ray detector for processing the x-ray image data into at least one tomosynthesis image of the region of the object.

20 Claims, 3 Drawing Sheets

U.S. PATENT DOCUMENTS

| | | | |
|---|---|---|---|
| 6,324,249 B1 | 11/2001 | Fazzio | 378/22 |
| 6,341,156 B1 * | 1/2002 | Baetz et al. | 378/98.8 |
| 6,345,194 B1 | 2/2002 | Nelson et al. | 600/425 |
| 6,442,288 B1 | 8/2002 | Haerer et al. | 382/128 |
| 6,611,575 B1 | 8/2003 | Alyassin et al. | |
| 2002/0080921 A1 | 6/2002 | Smith et al. | |
| 2002/0196895 A1 | 12/2002 | Plotz | 378/21 |
| 2004/0066882 A1 | 4/2004 | Eberhard et al. | 378/19 |

FOREIGN PATENT DOCUMENTS

| | | |
|---|---|---|
| EP | 0405862 A | 1/1991 |
| FR | 2 845 478 | 4/2004 |
| FR | 2845478 A | 4/2004 |

OTHER PUBLICATIONS

"Tomosynthesis Applied to Digital Substraction Angiography," Kruger et al., Radiology 152, pp. 805-808 (1984).

"Digital Tomosynthesis: Technique Modification and Clinical Applications for Neurovascular Anatomy," Radiology 152, pp. 719-724 (1984).

"Tomographic Digital Subtraction Angiography: Initial clinical Studies Using Tomosynthesis," Vries et al., Radiology 157, pp. 239-241 (1985).

"Development of a High-Resolution digital Tomosynthesis system and its Clinical Application," Kasuga et al., Radiographics 11(5), pp. 807-822 (1991).

"A Multiple Projection Method for Digital Tomosynthesis," Kolitsi et al., Med. Phys. 19(4), pp. 1045-1050 (1992).

"A Method for Selective Removal of Out-of-Plane Structures in Digital Tomosynthesis," Kolitsi et al., Med. Phys. 20(1), pp. 47-50 (1993).

"Chest Imaging with Dual-Energy substraction Digital Tomosynthesis," Sone et al., Acta Radiologica 34(4), pp. 346-350 (1993).

"Three-Dimensional Image Reconstruction by Digital Tomo-synthesis Using Inverse Filtering," Matsuo et al., IEEE Trans. Med. Imag. 12(2), pp. 307-313 (1993).

"Digital Angiosomosynthesis for Preoperative Evaluation of Cerebral Arteriobenous Malformations and Giant Aneurysns," Shigeta et al., AJNR 15, pp. 543-549 (1994).

"Digital Tomosynthesis Imaging of the Lung," Sone et al., Diagn. Radiol. 14(2), pp. 53-63 (1996).

Godfrey D J, et al.; "Practical Strategies for the Clinical Implementation of Matrix Inversion Tomosynthesis (MITS)", *Medical Imaging 2003: Physics of Medical Imaging*, San Diego, CA, Feb. 16-18, 2003, vol. 5030, pp 379-390.

Dobbins J T, et al.: "Digital X-Ray Tomosynthesis: Current State of the Art and Clinical Potential", *Physics in Medicine and Biology*, Taylor and Francis LTD, London, GB, vol. 48, No. 19, Oct. 7, 2003, pp. R65-R106.

French Search Report.

Godfrey, D.J. et al., "Practical Strategies for the Clinical Implementation of Matrix Inversion Tomosynthesis (MITS)", Medical Imaging 2003, Physics of Medical Imaging, San Diego, CA, USA, Feb. 16-18, 2003.

Dobbins, J.T., et al., "Digital X-ray Tomosynthesis: current state of the art and clinical potential", Physics in Medicine and biology, Taylor and Francis LTD, London, GB, vol. 48, No. 19, Oct. 7, 2003, pp. R65-R-106.

* cited by examiner

CONTINUOUS SCAN RAD TOMOSYNTHESIS SYSTEM AND METHOD

BACKGROUND OF THE INVENTION

The present invention relates generally to RAD tomosynthesis systems, and more specifically to a system and method for continuous scanning in RAD tomosynthesis systems.

RAD tomosynthesis systems are often used in the field of medicine to generate three-dimensional (3D) images of an object. A typical tomosynthesis system comprises an x-ray source, an x-ray detector, a motion controller and a processing circuit. The x-ray source is, typically, moved in a linear path and projects x-rays (x-ray radiation) on the object, usually a patient. The x-ray detector detects the x-rays and generates a corresponding tomosynthesis data set comprising projection radiographs. The processing unit processes the projection radiograph to generate a 3D image of the object.

One approach for projecting x-rays on the object is the step and shoot approach. In this approach, the x-ray source is moved along a linear path and pointed at a position on the object. X-rays are projected on the position and a projection radiograph is acquired. The x-ray source is then moved to a second position and a second projection radiograph is acquired. The x-ray source is thus moved to several positions relative to the object to acquire a set of projection radiographs. The projection radiographs are then processed to obtain a 3D image.

In general, it is desirable to keep the imaged object at a stationary position while acquiring the projection radiographs. To minimize object movement, the time required for the acquisition ("acquisition time") of the projection radiographs needs to be reduced. In the step and shoot method, the acquisition time is considerable large as the acquisition time is the sum of the exposure time for each position and the time taken by the x-ray source to move to various positions.

Another problem with the step and shoot approach is images generated are blurred due to system vibration. To reduce system vibration, a short period of time is required for residual vibration to dampen to an acceptable level before acquiring the projection radiograph. The short period of time further adds to the acquisition time, which is also undesirable.

It is therefore be desirable to minimize the acquisition time for generating 3D images by a tomosynthesis system while reducing the system vibration.

BRIEF SUMMARY OF THE INVENTION

Briefly, in accordance with one embodiment of the invention, an imaging system performing tomosynthesis on a region of an object comprises an x-ray source, motion controller, an x-ray detector and a processing unit. The x-ray source is positioned at a predetermined distance from the object and continuously moves along a linear path relative to the object. The x-ray source transmits x-ray radiation through the region of the object a plurality of predetermined locations along the path while the x-ray source is continuously moving along the path relative to the object. The motion controller is coupled to the x-ray source and continuously moves the x-ray source along the path relative to the object. The motion control of the x-ray source minimizes vibration in the imaging system due to continuous movement. The x-ray detector is positioned at a predetermined distance from the x-ray source. The x-ray detector detects the x-ray radiation transmitted through the region of the object, thus acquiring x-ray image data representative of the region of the object. The processing unit is coupled to the x-ray detector for processing the x-ray image data into at least one tomosynthesis image of the region of the object.

Another embodiment of the invention provides a method for generating a tomosynthesis image of a region of an object using an imaging system. The method comprises the a first step of continuously moving an x-ray source along a linear path positioned at a predetermined distance from the object wherein continuously moving the x-ray source minimizes vibration in the imaging system. In a second step, x-ray radiation is transmitted through the region of the object from a plurality of predetermined locations along the path while the x-ray source is continuously moving along the path relative to the object. The third step comprises detecting the x-ray radiation transmitted through the region of the object and the fourth step comprises acquiring x-ray image data representative of the region of the object. The fifth step comprises processing the x-ray image data into at least one tomosynthesis image of the region of the object.

In another embodiment, an imaging system is provided for performing tomosynthesis on a region of an object. The imaging system comprises an x-ray source positioned a predetermined distance from the object and continuously moving along a linear path relative to the object while transmitting x-ray radiation through the region of the object at a plurality of predetermined locations. A motion controller is coupled to the x-ray source and continuously moves the x-ray source along the path. Continuously moving the x-ray source minimizes vibration in the imaging system. An x-ray detector is positioned a predetermined distance from the x-ray source and detects the x-ray radiation transmitted through the region of the object. The x-ray detector acquires x-ray image data representative of the region of the object. A processing unit coupled to the x-ray detector processes the x-ray image data into at least one tomosynthesis image of the region of the object.

An alternative embodiment provides a method for generating a tomosynthesis image of a region of an object using an imaging system. The method comprises the steps of continuously moving an x-ray source along a linear path positioned a predetermined distance from the object wherein continuously moving the x-ray source minimizes vibration in the imaging system. The next step comprises transmitting x-ray radiation through the region of the object along the path at a plurality of predetermined locations while the x-ray source is continuously moving along the path relative to the object. The method further comprises the step of detecting the x-ray radiation transmitted through the region of the object, acquiring an x-ray image data representative of the region of the object and processing the x-ray image data into at least one tomosynthesis image of the region of the object.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

Figure 1:
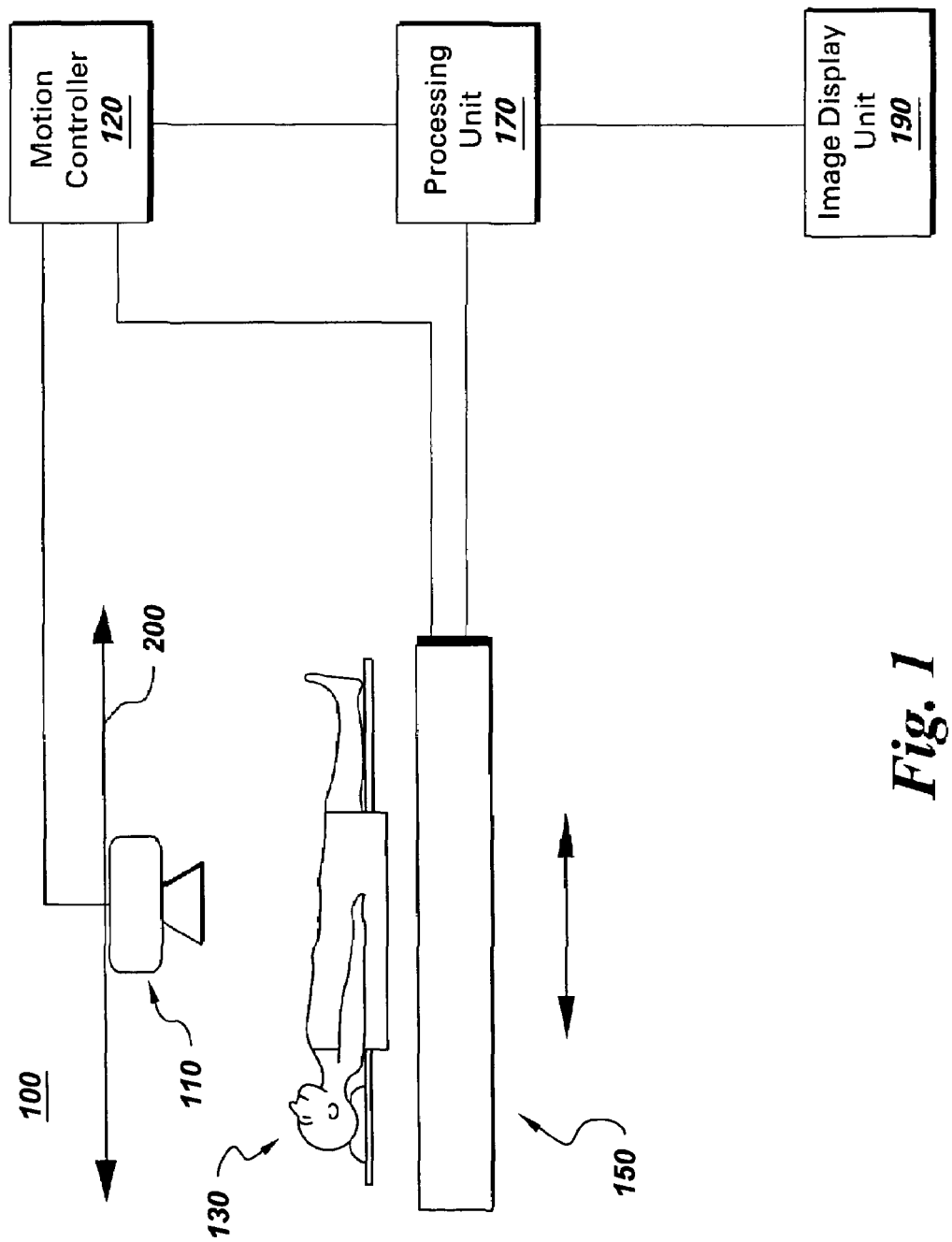
FIG. 1 is a diagrammatic view of an embodiment of an imaging system implemented in accordance with an aspect of the invention.

As shown in FIG. 1, an imaging system 100 includes an x-ray source 110 coupled to a motion controller 120. A processing unit 170 is coupled between the motion controller 120, x-ray detector 150 and the image display unit 190. It should be appreciated that the processing unit 170 can comprise a microprocessor, central processing unit, a personal computer, a workstation, a mini-computer, a mainframe computer or a supercomputer. It should also be appreciated that the motion controller 120 can be included in the processing unit 170 as software using a command language for movement of the x-ray source 110. It should further be appreciated that the processing unit 170 can be coupled to the motion controller 120, x-ray detector 150 and the image display unit 190 via, for example, a telephone or cable network, an ethernet, a local area network (LAN), or a wide area network (WAN), an integrated services digital network (ISDN), or a digital subscriber line (DSL). It should also be appreciated that the image display unit can comprise, for example, a video monitor, a liquid crystal display or other display monitor. Since the imaging system 100 continuously moves the x-ray source 110 during scanning and transmission of the x-ray radiation, costs associated with construction and components of such an imaging system 100 are typically less than that of convention imaging systems, such as step and shoot systems.

In one embodiment of operation, the x-ray source 110 is positioned at a predetermined distance from the x-ray detector 150 and a plane of the object 130. For example, the predetermined distance is a fixed distance that remains constant throughout the x-ray imaging process (scanning). In another embodiment, the predetermined distance can vary relative to x-ray detector 150 and/or the object 130 as the x-ray source 110 moves along path 200. For example, the predetermined distance can vary as the x-ray source 110 is moved along the path 200 relative to the object 130 if the object 130 has an irregular or varying shape/profile with respect to the path 200. The x-ray source 110 is instructed by the motion controller 120 to move continuously along a path 200 relative to the object 130 and transmits x-ray radiation (x-rays) through different regions of object 130. The motion controller 120 is coupled to the x-ray source 110 and controls the continuous movement of the x-ray source 110 along the path 200 relative to the object 130. In one embodiment, the x-ray source 110 is articulated wherein the x-ray source 110 points to a common and/or fixed spot on or in relation to the object 130. It should be appreciated that the object can comprise a human being, animal or other objects (organic or inorganic), such as, mechanical/metallic components or luggage. It should further be appreciated that the x-ray source 110 can be adapted to move along any axis relative to the object 130 by repositioning the object 130 and/or the imaging system 100 with respect to one another. For example, the path 200 can move from head to toe or from shoulder to shoulder when the object 130 comprises a patient. Since the x-ray source 110 continuously moves relative to the object 130, vibration in imaging system 100 associated with starting and stopping the x-ray source 110 at various points is substantially reduced. A further advantage of the imaging system 100 is that continuous movement of the x-ray source 110 reduces the scanning time for the object 130. Therefore, any misrepresentations in the image data caused by movement of the object 130 during the exposure time are reduce because the total acquisition time is reduced compared to conventional systems, such as step and shoot systems.

As the x-ray source 110 is continuously moved over the object 130, the x-ray detector 150 detects the x-ray radiation transmitted from the x-ray source 110 and through the object 130 at various regions. Correspondingly, the x-ray detector 150 acquires an x-ray image data representative of the regions of the object 130. Typically, the x-ray source 110 is positioned at a predetermined distance from x-ray detector 150. In one embodiment, the x-ray detector 150 is stationary relative to the object 130 before, after and/or during exposure of the object 130 to the x-rays from the x-ray source 110. In another embodiment, the x-ray detector 150 is capable of moving relative to the object 130 before, after and/or during exposure of the object 130 to the x-rays from the x-ray source 110. In this embodiment, the x-ray detector 150 is connected to the motion controller 120. Further, in this embodiment, the x-ray detector 150 can be adapted to move linearly with the x-ray source 110 or in other patterns, such as, one dimensional, two dimensional and/or three dimensional paths relative to the x-ray source 110. It should be appreciated that the x-ray detector 150 can comprise a digital x-ray detector, a RAD detector or a flat panel detector.

The processing unit 170 is coupled to the x-ray detector 150 and processes x-ray image data (for example, a plurality of x-ray projections) that is detected by the x-ray detector 150 to generate a corresponding tomosynthesis image of the region and/or regions of the object 130. The generation of the tomosynthesis image involves reconstruction of the x-ray image data (x-ray projections) into a three-dimensional (3D) volume that is representative of the object 130 that is scanned. In one embodiment, the tomosynthesis image is displayed to a user through image display unit 190. As generally described above, the processing unit 170 also generates control signals to the motion controller 120 to control the motion of x-ray source 110. Some exemplary manners in which the motion controller 120 can move the x-ray source 110 along the path 200 relative to the object 130 are described in further detail hereinbelow.

Figure 2:
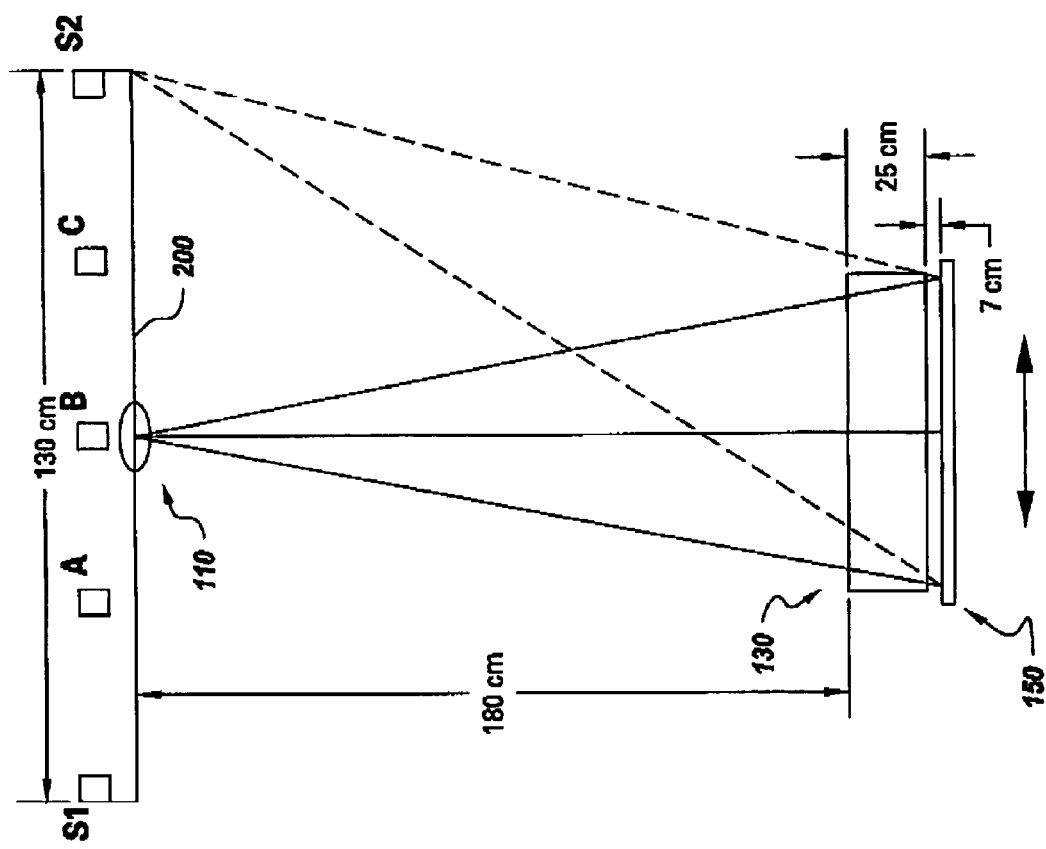
FIG. 2 is a diagrammatic view illustrating the motion of the x-ray source relative to the object in one embodiment of imaging system.

In FIG. 2, the motion of the x-ray source 110 relative to the object 130 is provided where the x-ray source 110 moves above the object 130. It should be appreciated that the path 200 that the x-ray source 110 moves along can comprise a linear path (straight line) over and above the object 130. In one embodiment where the object 130 comprises a human patient, the x-ray source 110 moves linearly along the long axis (head to toe) of the patient. As shown in FIG. 2, in one embodiment, the x-ray detector 150 is positioned below the object 130. It should further be appreciated, in other embodiments, that the x-ray source 110 can also move in one dimensional, two dimensional and/or three dimensional paths relative to the x-ray detector 150 during scanning.

The x-ray source 110 is positioned at a predetermined distance from the object 130. In one embodiment, the predetermined distance equals about 180 centimeters (cm). The x-ray source 110 moves continuously moving along the path 200 relative to the object 130. In one embodiment, the x-ray source 110 is continuously moved at a predetermined velocity from point S1 to point S2. It should be appreciated that the term continuous movement is defined as movement by the x-ray source 110 from point S1 to point S2 without stopping. In one embodiment, the distance that the x-ray source 110 travels between point S1 and point S2 is 130 cm. The x-ray source 110 transmits x-ray radiation through regions of the object 130 at predetermined locations A, B and C respectively along the path 200 while the x-ray source 110 continuously moves along the path 200 from point S1 to point S2 relative to the object 130. In this embodiment, when the x-ray source 110 is at locations other than predetermined locations A, B and C, the x-ray source 110 is not instructed to transmit x-rays. For example, in one embodiment, the scan time required for the x-ray source 110 to move from point S1 to S2 is about 5 second. As further shown in FIG. 2, in one embodiment, the object 130 has a depth or thickness of about 25 cm and the x-ray detector 150 is located about 7 cm below the object. In this embodiment, the average velocity of the x-ray source 110 during the scanning is about 26 cm/sec. The amount of time that the x-ray source 110 transmits x-rays thought the object 130 (exposure time) at each of the predetermined locations is about 2.5 milliseconds (msec) that corresponds to a x-ray source moving about 0.65 mm during exposure. In this embodiment with the aforementioned speeds and dimensions, a maximum blurring at the x-ray detector 150 is about 0.12 millimeter (mm) or roughly one-half (½) of a pixel when the x-ray detector 130 comprises a RAD detector. It should be appreciated that a blurring of this amount (about 0.12 mm or ½ of a pixel) has virtually no impact on the quality of the x-ray image data. The x-ray detector 150 detects the x-ray image data from the x-ray that are transmitted through the object 130 at the predetermined locations A, B and C. It should further be appreciated that the x-ray source 110 can transmit x-ray radiation at more or less predetermined locations than shown in FIG. 2. In another embodiment, the x-ray detector 150 acquires x-ray image data at predetermined time intervals during the continuous movement of the x-ray source 110 from point S1 to point S2. It should be appreciated that, in this embodiment, the predetermined time intervals that the x-ray detector 150 acquires the x-ray image data can correspond to times when the x-ray source 110 is positioned at predetermined locations, for example, points A, B and C.

In another embodiment, motion controller 120 moves the x-ray source 110 at different velocities as the x-ray source 110 continuously moves from point S1 to point S2. In this embodiment, the x-ray source 110 moves, for example, at a first velocity from point S1 to point A. When the x-ray source 110 reaches point A, the x-ray source moves at a second velocity for a predetermined amount of time. In one embodiment, the exposure time at each point is about 2.5 msec. Further, after the x-ray source 110 has moved at a second velocity for the predetermined time, the x-ray source 110 can again move at the first velocity from point A to point B. Again, once the x-ray source 110 reaches point B, the x-ray source 110 can move the second velocity for a predetermined time. After the predetermined time has elapsed, the x-ray source 110 can move at the first velocity from point B to point C. Once the x-ray source 110 reaches point C, the x-ray source 110 moves at the second velocity for a predetermined time. After the predetermined time has elapsed, the x-ray source 110 can move from point C to point S2 at the first velocity, and then the x-ray source 110 can stop at point S2. In one embodiment, the x-ray source 110 can transmit x-rays while it is moving at the second velocity, and the x-ray detector 150 acquires the x-ray image data while the x-ray source is moving at the second velocity. In another embodiment, the x-ray source 110 continuously transmits x-rays as it moves along path 200. In one aspect of this embodiment, the x-ray detector 150 continuously acquires x-ray image data as the x-ray source 110 moves along the path 200 transmitting x-rays. In another aspect of this embodiment, the x-ray detector 150 acquires images at predetermined times, and the predetermined times correspond to times when the x-ray source 110 is moving at the second velocity. In one embodiment, the first velocity is greater than the second velocity. It should be appreciated that, in other embodiments, the x-ray source 110 can be moved at a variety of velocities as it is continuously moved from point S1 to point S2. In one embodiment, the first velocity can range from about 20 cm/sec to about 26 cm/sec and the second velocity can comprise about half the first velocity. In a further embodiment, the first velocity comprises a velocity greater than about 26 cm/sec (26 cm/sec plus a predetermined delta) and the second velocity comprises a velocity of about 13 cm/sec. In other embodiments, the first velocity and the second velocity need not be the same at the various predetermined locations along the path 200. It should further be appreciated that in other embodiments that the transition between the first velocity to the second velocity and the second velocity to the first velocity involves a transition deceleration and acceleration, respectively, of the x-ray source 110 to minimize vibration in the imaging system 100.

In other embodiments, the first velocity and the second velocity need not be the same at the various predetermined locations along the path 200. In one embodiment, the time between the transmission of x-rays by the x-ray source 110 corresponds at least to the read-out time of the x-ray detector 150. For example, the x-ray detector 150 read out time can range between 125 to 180 msec, and, therefore, the first velocity can be reduced by a factor of about 2 or more to obtain the second velocity during the x-ray transmission time with minimal impact on the velocity between the transmissions. In another embodiment, a high power x-ray source 110 can also reduce blurring caused by moving the x-ray source 110 while transmitting x-rays because the high power x-ray source 110 allows the required x-ray exposure to be delivered in a time less than 2.5 msec. One example of a high power x-ray source 110 can comprise an x-ray tube having a power ranging a power ranging from about 20 to about 30 kilowatts (kW). In another example, a high power x-ray source 110 comprises an x-ray tube having a power of about 64 kW.

Figure 3:
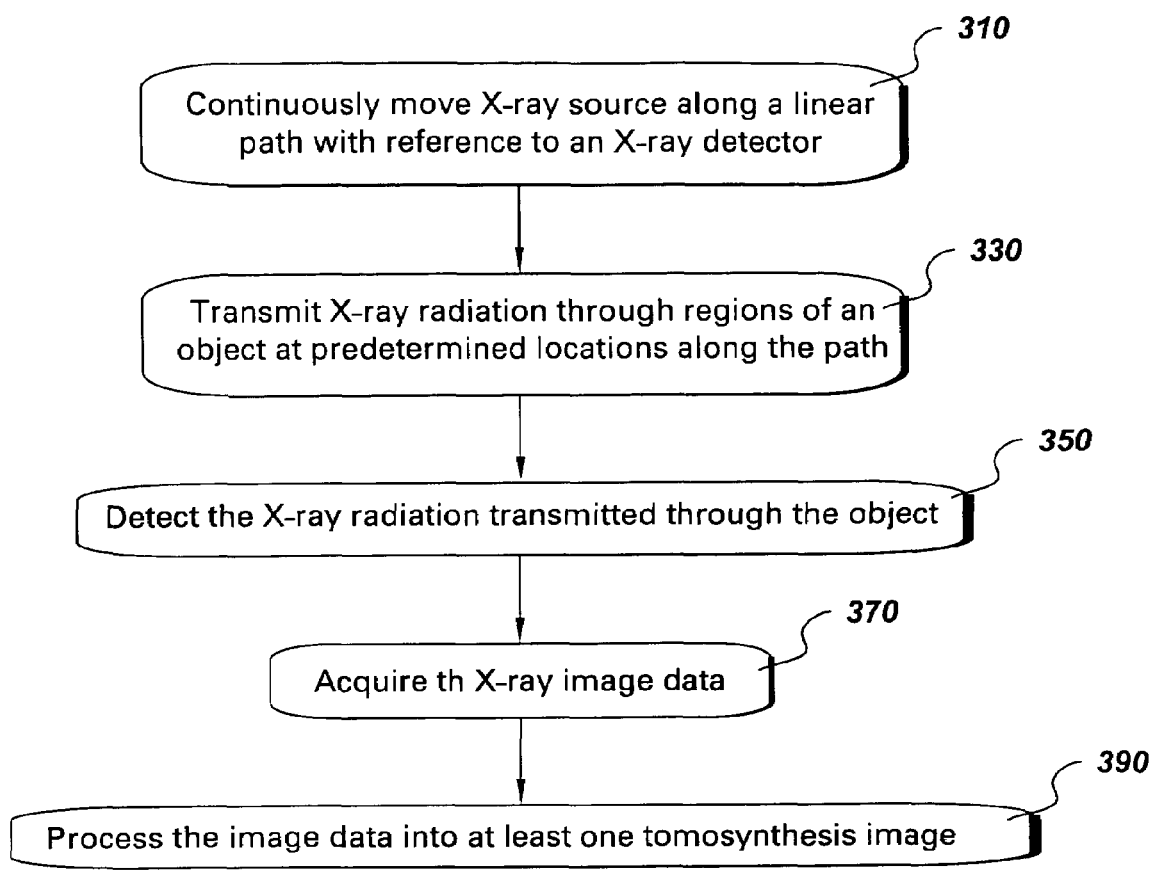
FIG. 3 is a flow chart illustrating the general method for generating a tomosynthesis image

As shown in FIG. 3, a method for continuously moving an x-ray source 110 about an object 130 to acquiring x-ray image data is provided. The x-ray source 110 is moved continuously along a linear path with reference to the detector 200 (step 310). The x-ray source 110 is positioned at a predetermined distance from the object 130. By continuously moving, the x-ray source 110 linearly along the path 200, vibrations in the imaging system 100 are minimized because the x-ray source 110 is not stopped and restarted along the path 200. X-ray radiation is transmitted through a region of the object 130 (step 330). In one embodiment, the x-ray radiation is transmitted from the x-ray source 110 when the x-ray source 110 reaches a plurality of predetermined locations along the path 200. In another embodiment, the x-ray radiation is transmitted from the x-ray source 110 and through the region of the object 130 as the x-ray source 110 is continuously moving along the path 200 relative to the object 130. The x-ray detector 150 detects the x-ray radiation that is transmitted through the region of the object 130 (step 350). A processing unit 170 acquires an x-ray image data representative of the region of the object 130 (step 370). The processing unit 170 processes the x-ray image data into at least one tomosynthesis image of the region of the object 130 (step 390).

As described hereinabove, the image blurring caused due to vibration of the imaging system 100 is reduced when compared to conventional step and shoot systems and methods. Further, blurring could be caused because the x-ray source 110 is moving while the x-ray detector 150 is acquiring the x-ray image data, but such blurring can be reduced or eliminated by decreasing the x-ray transmission time during scanning. However, the tomosynthesis image generated may be blurred due to various other factors such as vibration due to the motion of the x-ray source 110, vibration caused by motion of the x-ray detector 150, and movement of the object 130 during scanning. Typically, movement of the object 130 during scanning can be characterized in three types of movement when the object 130 comprises a patient. Such movement can be termed gross movement (large movement of the patient), cardiac movement (beating of the heart) and respiratory movement (movement of the lungs). All types of movement can cause misrepresentations of the patient structures during algorithm reconstruction, but gross movement is one of the most troublesome. The imaging system 100 uses continuous movement of the x-ray source 110 to reduce the overall acquisition time, and therefore, reduce the total time available for the patient to move. As such, the imaging system 100 provides an advantage to other systems by reducing the total acquisition time that can reduce the number of misrepresentations of patient structures caused by movement of the patient.

As described hereinabove, such blurring in the x-ray image data can be reduced by varying the speed that the x-ray source 110 travels when the x-ray image data is being acquired by the x-ray detector 130. Typically, the blurring caused by motion of the x-ray source 110 can be characterized using the speed of the moving x-ray source 110, the geometry of the imaging system 100 and the known characteristics of the imaged object, such as, x-ray absorption characteristics. Typically, moving the x-ray detector 150 eliminates and/or allows controlling of blurring caused during scanning caused by the x-ray source 110 moving during scanning. In one embodiment, moving the x-ray detector 150 as well as the x-ray source 110 can reduce blurring caused by motion of the x-ray source 110. In one embodiment, the x-ray detector 150 is moved when the x-ray source 110 is transmitting x-rays. In another embodiment, the x-ray detector 150 can continuously move with the x-ray source 110. In even another embodiment, the tomosynthesis images generated using the acquired x-ray image data and/or the resulting tomosynthesis image can be deblurred using various data reconstruction techniques.

The foregoing discussion of the invention has been presented for purposes of illustration and description. Further, the description is not intended to limit the invention to the form disclosed herein. Consequently, variations and modifications commensurate with the above teachings and with the skill and knowledge of the relevant art are within the scope of the present invention. The embodiment described herein above is further intended to explain the best mode presently known of practicing the invention and to enable others skilled in the art to utilize the invention as such, or in other embodiments, and with the various modifications required by their particular application or uses of the invention. It is intended that the appended claims be construed to include alternative embodiments to the extent permitted by the prior art.

What is claimed is:

1. An imaging system for performing tomosynthesis on a region of an object, said imaging system comprising:
   an x-ray source positioned a predetermined distance from said object and continuously moving along a linear path relative to said object, said x-ray source transmitting x-ray radiation through said region of said object a plurality of predetermined locations along said path while said x-ray source is continuously moving along said path relative to said object;
   a motion controller coupled to the x-ray source and continuously moving said x-ray source along said path relative to said object wherein continuously moving said x-ray source minimizes vibration in said imaging system, and wherein said motion controller moves said x-ray source at a first velocity at said plurality of predetermined locations along said pert and said motion controller moves said x-ray source at a second velocity outside said plurality of predetermined locations along said path, and wherein the second velocity is different from the first velocity;
   an x-ray detector positioned a predetermined distance from said x-ray source, the x-ray detector detecting said x-ray radiation transmitted through said region of said object, said x-ray detector acquiring x-ray image data representative of said region of said object wherein said x-ray image data is acquired by said x-ray detector at a rate relative to said moving x-ray source; and
   a processing unit coupled to said x-ray detector for processing said x-ray image data into at least one tornosynthesis image of said region of said object.

2. The imaging system of claim 1 wherein said x-ray image data comprises a plurality of low dose projection radiographs.

3. The imaging system of claim 1 wherein said processing unit performs a deblurring operation on said x-ray image data to reduce the effects of blurring caused at least by continuously moving said x-ray source.

4. The imaging system of claim 1 wherein exposure time of transmitting said x-ray radiation through said region of said object at said plurality of predetermined locations is a predetermined time.

5. The imaging system of claim 4 wherein said predetermined time is 2.5 milliseconds.

6. The imaging system of claim 1 wherein the x-ray detector comprises a RAD x-ray detector.

7. The imaging system of claim 1 wherein said x-ray detector is connected to the motion controller and is selectively movable relative to said object.

8. The imaging system of claim 1 wherein said x-ray detector is stationary relative to said object.

9. The imaging system of claim 1 wherein said predetermined distance that said x-ray source is positioned relative to a plane of said object comprises a fixed distance.

10. The imaging system of claim 1 wherein said x-ray source comprises an x-ray tube.

11. A method for generating a tomosynthesis image of a region of an object using an imaging system, said method comprising the steps of:
   continuously moving an x-ray source along a linear path positioned a predetermined distance from said object wherein continuously moving said x-ray source minimizes vibration in said imaging system;
   transmitting x-ray radiation through said region of said object from a plurality of predetermined locations along said path while said x-ray source is continuously moving along said path relative to said object, wherein continuously moving said x-ray source comprises continuously moving said x-ray source at a first velocity at said plurality of predetermined locations along said path; and continuously moving said x-ray source at a second velocity outside said plurality of predetermined locations along said path, and wherein the second velocity is different from the first velocity;

detecting said x-ray radiation transmitted through said region of said object;

acquiring x-ray image data representative of said region of said object, wherein said x-ray image data is acquired at a rate relative to said moving x-ray source; and processing said x-ray image data into at least one tomosynthesis image of said region of said object.

12. The method of claim 11 wherein said x-ray image data comprises several low dose projection radiographs.

13. The method of claim 11 further comprising the step of performing a deblurring operation on said x-ray image data to reduce the effects of blurring caused at least by continuously moving said x-ray source.

14. The method of claim 11 wherein the step of transmitting said x-ray radiation comprises transmitting said x-ray radiation for a predetermined time at said plurality of predetermined locations.

15. The method of claim 14 wherein said predetermined time comprises about 2.5 milliseconds.

16. The method of claim 11 wherein said step of detecting said x-ray radiation comprises using an x-ray detector to detect said x-ray radiation.

17. The method of claim 16 wherein said x-ray detector comprises a RAD x-ray detector.

18. The method of claim 16 further comprising the step of selectively moving said x-ray detector relative to said object.

19. The method of claim 16 wherein said x-ray detector remains stationary relative to said object.

20. The method of claim 11 wherein said predetermined distance that said x-ray source is positioned relative to a plane of said object comprises a fixed distance.

* * * * *